United States Patent [19]

Scheinthal et al.

[11] 4,325,908
[45] Apr. 20, 1982

[54] THEOPHYLLINE TEST

[75] Inventors: Bernard M. Scheinthal, Pine Brook; Lester Chafetz, New Providence, both of N.J.

[73] Assignee: Warner-Lambert Company, Morris Plains, N.J.

[21] Appl. No.: 122,912

[22] Filed: Feb. 20, 1980

[51] Int. Cl.³ .................... G01N 21/78; G01N 33/52
[52] U.S. Cl. .................... 422/61; 23/230 B; 23/929; 252/408
[58] Field of Search ........... 23/230 B, 905, 929; 422/61; 252/408

[56] References Cited

U.S. PATENT DOCUMENTS

| | | | |
|---|---|---|---|
| 2,418,033 | 3/1947 | Kamlet | 23/230 B X |
| 3,449,081 | 6/1969 | Hughes | 422/61 |
| 3,585,004 | 6/1971 | Mast | 23/230 B X |
| 3,955,926 | 5/1976 | Fischer | 422/56 X |

OTHER PUBLICATIONS

Truitt et al., J. of Pharmacology & Experimental Therapeutics 91, (1947), pp. 185–189.
Truitt, Jr. et al., "The Quantitative Estimation of Theophylline in Blood", Chem. Abstr., vol. 42, No. 630h, 1948.
Gerhard et al., "Indirect Plasma–Theophylline Monitoring in Asthmatic Children by Det. of Theophylline Conc. in Saliva", Chem. Abstr., vol. 81, 1974, No. 130743c.

*Primary Examiner*—Arnold Turk
*Attorney, Agent, or Firm*—Albert H. Graddis

[57] ABSTRACT

Theophylline concentrations in body fluids can be determined by a color reaction. The theophylline is converted to theophyllidine by reaction with an alkali such as sodium or potassium hydroxide at an elevated temperature and, after neutralization of the alkali with an organic acid, the theophyllidine formed is coupled with a chromogen to yield a color whose depth is proportional to the theophylline concentration in the body fluid being tested. The improved procedure utilizes a solid alkali for the heating step and a non-corrosive acid for the neutralization. An improved chromogen yields a bright, relatively stable purple color.

3 Claims, 1 Drawing Figure

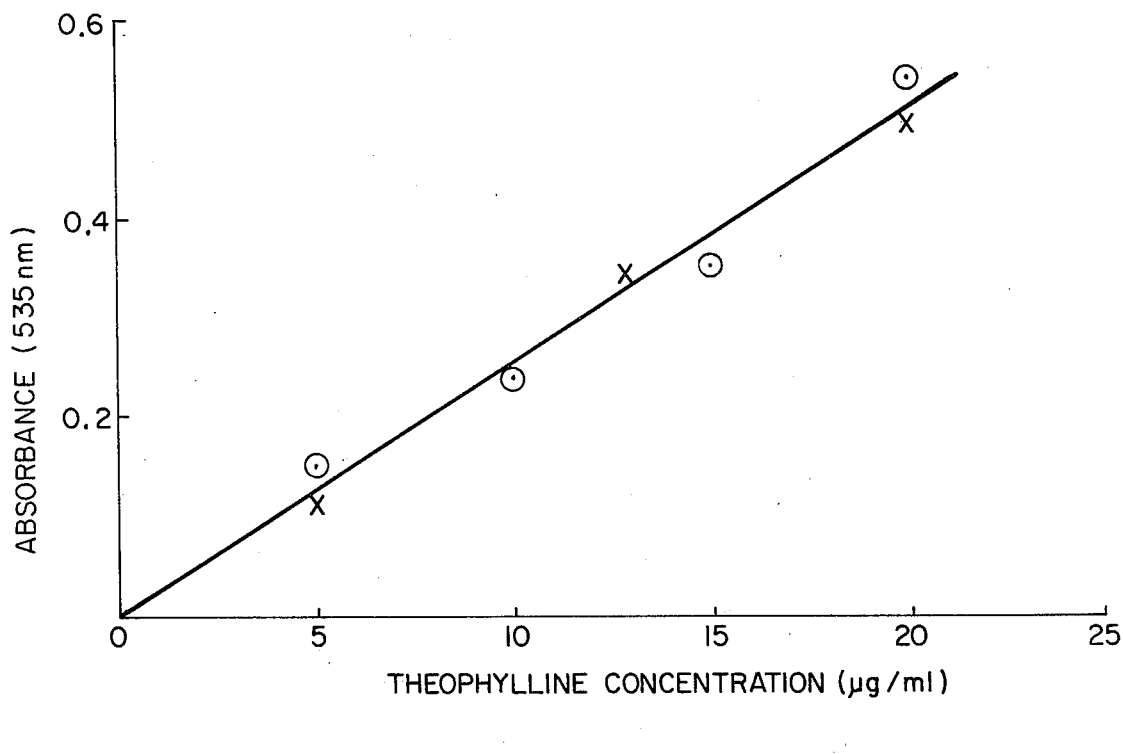

THEOPHYLLINE TEST

The present invention relates to an improved test for the qualitative and quantitative detection of theophylline in body fluids such as blood and saliva.

BACKGROUND OF THE INVENTION

Theophylline finds important therapeutic application in the management of the asthmatic patient. It is useful not only as a prophylactic drug but also in the treatment of asthmatic attacks. Studies have revealed that blood levels of theophylline of as little as 5, but generally of 10 to 20 $\mu$g/ml are closely associated with observed therapeutic effects. Thus, patient monitoring and the regular determination of blood levels in the patient is an important adjunct to successful theophylline therapy. By noting blood theophylline levels in either blood serum or blood plasma the physician can determine, firstly, whether the patient under examination is following the prescribed dosage regimen and, secondly, whether this regimen is achieving the necessary blood levels for the desired therapeutic effect. A quick, accurate and reliable test which can be carried out as a routine office procedure by the physician or a technical assistant and is not dependent upon the use of high technology and sophisticated equipment such as that required for radioimmunoassay or high pressure liquid chromatography would be of wide utility.

Accordingly, an important object of this invention is to provide an improved test procedure for the qualitative and quantitative determination of theophylline levels in body fluids.

Another object of this invention is to provide a test procedure for determining levels of theophylline in body fluids which can be carried out conveniently as a routine procedure and which is capable of yielding accurate, dependable results.

Other objects of this invention will be apparent from the following detailed description.

DESCRIPTION OF THE PRIOR ART

As previously disclosed by Truitt et al, in the Journal of Pharmacology and Experimental Therapeutics 91, (1947), pages 185–189, when theophylline is treated by boiling with a strong aqueous alkali, it yields the reaction product theophyllidine which can be coupled with an azo compound to yield a colored product. In particular, using Fast Blue 2B salt as the diazo coupling agent, which salt is a zinc chloride complex of diazotized 5-amino-2-benzoyl-amino-1,4-diethoxybenzene, and coupling it with the theophyllidine obtained by boiling theophylline with 50% aqueous potassium hydroxide, a stable red color is obtained. The depth of this color can be utilized to reach a quantitative estimate of initial theophylline concentration.

The procedure for determining blood theophylline levels recommended by Truitt et al involves the hemolysis of the red blood cells and treatment with sodium tungstate to yield a clear liquid which is evaporated to dryness. After a multistage chloroform extraction of the residue to extract the theophylline present and the boiling of the theophylline thus extracted with 50% aqueous KOH as described, the alkali boiling step is followed by neutralization of the alkali present with 50% glacial acetic acid. The mixture obtained is cooled and the theophyllidine formed is coupled with the particular azo compound Fast Blue 2B, the zinc chloride complex of diazotized 5-amino-2-benzoyl-amino-1,4-diethoxy benzene. The intensity of the red color which is formed can be read in a suitable photometer. Comparison of the absorption observed with a suitably prepared standardized curve relating to absorption at known theophylline concentrations enables the theophylline concentration in the blood sample to be determined. The overall time required for this test procedure is 45 minutes.

SUMMARY OF THE INVENTION

We have now found, however, the determination of the theophylline concentration in blood plasma or blood serum, or in saliva may be greatly simplified and carried out rapidly and safely with no compromise in the accuracy of the results. This improvement may be obtained if, instead of boiling the reaction mixture of theophylline and alkali hydroxide, heat for the reaction is provided by the heat of solution of the alkali hydroxide in the aqueous solution of theophylline being tested by adding solid particles or pellets of alkali hydroxide to the aqueous solution or vice versa, and then neutralizing the unreacted alkali hydroxide with a slight excess of a solid organic acid. By then coupling the theophyllidine reaction product in the resulting acid solution with a stable chromogen such as Fast Blue B, i.e., the zinc chloride double salt of tetrazotized o-anisidine, a stable purple color is obtained whose depth is proportional to the initial theophylline concentration.

When standardized quantities of reactants and reagents are employed the stable purple color produced may be read on a photometer to give a quantitative result by determining absorbance at a wave length 540 nm. Comparison of this absorbance to a standard curve constructed on the basis of aqueous solutions containing known quantities of theophylline enables the theophylline concentration to be determined on a quantitative basis since the depth of color observed and the absorbance is proportional to the concentration of the theophylline in the body fluid being tested.

The test with saliva requires only about 0.5 ml and is extremely useful in obtaining an immediate qualitative answer to the question of whether or not an asthmatic patient is complying with the theophylline therapy prescribed. The theophylline blood level may be established from the saliva test if the quantitative saliva concentration is first determined and this value is then multiplied by a factor of 2. The relative saliva to blood level ratio of theophylline in these body fluids is usually in the area of about 0.48–0.5. However, depending upon the individual, this ratio can vary from 0.3 to 0.7 with the average being about 0.5. Even considering that such individual variations do exist, it can be seen that the test procedure described provides a readily available non-invasive technique for determining fairly accurately and rapidly whether a particular theophylline dosage regimen in a particular patient is providing a therapeutic blood level of theophylline of the order of 5 to 20 $\mu$g/ml after this ratio is established.

The use of the alkali hydroxide in solid form to achieve the necessary reaction temperature through the heat of solution of the particles in the aqueous theophylline medium so that the theophylline present will be converted to theophyllidine lends substantially greater convenience and utility to the procedure than that afforded by the prior art. The alkali hydroxide particles can be prepackaged in the appropriate quantity needed for the reaction and the handling and pouring of 50% aqueous caustic solutions of sodium or potassium hydroxide is avoided. Substantial advantages are also obtained by use of a solid organic acid to neutralize the excess alkali hydroxide remaining in the reaction medium after the conversion of the theophylline to theophyllidine. Since the subsequent azo coupling reaction takes place in an acid medium it is very helpful in simplifying the procedure to premeasure and prepackage the organic acid for the neutralization step so that when slowly added to the alkali hydroxide reaction medium all of the base will be neutralized and only a slight excess of acid will remain to provide an acid medium for the azo coupling reaction. These expedients greatly simplify the procedure so that it may then be carried out by relatively inexperienced and untrained office assistants without any loss in the reliability and accuracy of the test procedure.

The accuracy and reliability of the novel test procedure described is substantially enhanced by employing as the chromogen in the coupling reaction the stabilized zinc chloride salt of tetrazotized dianisidine. This tetrazotized compound, also known as Fast Blue B, yields a bright stable purple chromophor when coupled with the theophyllidine present and the resulting depth of color is an accurate indication of the level of theophyllidine present.

The ease and convenience of the test procedure in determining theophylline blood levels can be greatly enhanced by the use of a small-scale or miniaturized reverse phase partition chromatography column for isolating the theophylline from other components in the blood serum or blood plasma being tested. While the prior art procedure relies upon a complex separation procedure involving evaporation of the serum followed by several chloroform extractions and a final evaporation, it has been found that by the use of a miniaturized reverse phase partition chromatography column for treating a blood plasma sample a very precise separation of the theophylline present in the plasma can be effected.

A particularly useful miniaturized column for this purpose is one which contains the $C_{18}$ compound octadecylsilane bonded to silica gel which is available in a cartridge form and which may be used as an adjunct or accessory to a hypodermic syringe. These cartridges are available commercially as the $C_{18}$ Sep-Pak cartridge from Water Associates, Inc., Milford, MA 01757.

To obtain a quantitative determination of a theophylline blood level using this column chromatography procedure the partition column is prepared by first connecting a cartridge to the end of a Luer tip syringe, then pumping a small amount of methanol through the column followed by a water wash. A measure sample of blood serum or plasma is then pumped through the syringe and the column and theeffluent discarded. The theophylline present is retained on the column. A water wash of the column removes all of the soluble blood components and is discarded. The theophylline present is extracted from the column by a methanol wash, the methanol removed by heating and then water and solid particles of sodium hydroxide or potassium hydroxide are added to the aqueous theophylline. After about five minutes the alkali is neutralized with a solid organic acid and the solution cooled. Suitable solid organic acids are citric, tartaric, maleic, malonic, fumaric and succinic acid. Addition to the slightly acid solution of a measured amount of Fast Blue B solution in methanol followed by mixing produces a purple color as the reaction product whose absorbance is then read after 5 minutes at 535 nm. A substantially linear relationship between absorbance and theophylline concentration exists as shown in the accompanying FIGURE.

In order to further illustrate this invention the following Examples are given:

EXAMPLE I

Fast Blue B Solution:

Shake about 400 mg Fast Blue B salt with 100 ml methanol for about 15 minutes in a 250 ml stoppered Erlenmeyer flask. Filter the solution thru S&S No. 508 charcoal impregnated filter paper, 12.5 cm. The solution should be prepared fresh once a week.

EXAMPLE II

Qualitative Test for Compliance

To 0.5 ml saliva from a patient on theophylline therapy which has been introduced into an $18 \times 150$ mm test tube, add 0.5 ml water and $0.75 \pm 0.05$ gms sodium hydroxide pellets. Shake vigorously for about 5 minutes. Cautiously add 1.5 gms citric acid and 1.0 ml water. Mix gently to avoid sudden evolution of carbon dioxide. Cool to room temperature. Add 0.5 ml Fast Blue B reagent, mix well on a vortex mixer and allow to stand for 5 minutes. Read the absorbance at about 540 nm versus a blank and/or compare with a standard.

EXAMPLE III

Preparation of Chromatography Column

Remove the plunger from a 10 ml Luer Tip syringe. Connect the longer end of a $C_{18}$ Sep-Pak cartridge firmly onto the Luer Tip. Add 5 ml methanol to the syringe barrel and use the plunger to pump the solvent through the cartridge. Discard the effluent. Repeat the wash step but carry out the wash employing 5 ml of water. With the cartridge connected to the syringe add 0.5 ml of blood serum from a patient on theophylline therapy to the syringe and use the plunger to pump the serum through the cartridge. Discard the effluent. Repeat this step employing 5 ml of water and discard the effluent. Then pipet 2 ml methanol into the syringe barrel and pump the methanol through the cartridge. Discard the first 6 drops and collect the balance of the effluent in a 18 mm $\times$ 150 test tube.

EXAMPLE IV

The collected effluent from Example III is dried by blowing nitrogen gas over the solution and/or heating with warm water. 0.5 ml water is added to the residue and $0.40 \pm 0.05$ g sodium hydroxide pellets. Shake for above five minutes. Add very carefully, 0.8 g citric acid and 1.0 ml water. Shake very gently. Cool to room temperature. Add 0.3 ml Fast Blue B solution. Mix well on a vibrating mixer such as the Vortex Genie ®. After about 5 minutes, read absorbance at about 540 nm. Fast Blue B reacts quickly with the theophyllidine to form a purple chromophore in 3 to 5 minutes. The maximum absorbance of the dye is between 535 and 540 nm. After about 30 minutes, 25% of the absorbance is lost, so the reading should be taken within a short time after color formation.

This reaction is quite specific to theophyllidine. It has been found that solutions containing concentrations even as large as about 1 mg/ml of compounds such as urea, phenobarbital, allantoin, hypoxanthine, xanthine, 1-methylxanthine, 3-methylxanthine, 7-methylxanthine and theobromine do not react with Fast Blue B. Similar concentrations of caffeine, beta-hydroxypropyl theophylline and beta-hydroxyethyltheophylline do react with Fast Blue B to form a colored product which although initially purple fades rapidly to a yellow color usually in less than 5 minutes.

We claim:

1. A diagnostic test kit for the determination of theophylline levels in a body fluid, comprising in combination (a) a vessel in which is placed a predetermined measured volume of body fluid containing theophylline values, (b) an alkaline hydroxide in solid particulate form in an amount whose heat of solution when combined with said predetermined volume of body fluid is sufficient to raise the temperature of said fluid to a temperature at which reaction with said alkaline hydroxide acts to hydrolyze any theophylline present to theophyllidine, (c) a solid organic acid in stoichiometric excess relative to said alkaline hydroxide, and (d) a tetrazo chromogen which is a stabilized salt of tetrazotized dianisidine.

2. A diagnostic kit in accordance with claim 1 in which the alkaline hydroxide is sodium hydroxide, the organic acid is a dicarboxylic acid and the chromogen is a zinc chloride salt of tetrazotized dianisidine.

3. A diagnostic kit in accordance with claim 2 in which the organic acid is citric acid.

* * * * *